United States Patent [19]
Belk et al.

[11] Patent Number: 5,969,260
[45] Date of Patent: Oct. 19, 1999

[54] REMOTELY INTERROGATABLE APPARATUS AND METHOD FOR DETECTING DEFECTS IN STRUCTURAL MEMBERS

[75] Inventors: John H. Belk, St. Louis; Edward V. White, St. Charles, both of Mo.

[73] Assignee: McDonnell Douglas Corporation

[21] Appl. No.: 09/050,719

[22] Filed: Mar. 30, 1998

[51] Int. Cl.$^6$ .................................................. G01B 7/16
[52] U.S. Cl. ................................................. 73/773; 73/775
[58] Field of Search .............................. 73/773, 775, 781, 73/799, 804, 808, 810, 811, 774, 763

[56] References Cited

U.S. PATENT DOCUMENTS

| | | | |
|---|---|---|---|
| 4,566,339 | 1/1986 | Davidson et al. | 73/862.392 |
| 4,803,886 | 2/1989 | May et al. | 73/862.392 |
| 5,195,046 | 3/1993 | Gerardi et al. | 73/583 |
| 5,446,445 | 8/1995 | Bloomfield et al. | 340/521 |
| 5,814,816 | 9/1998 | Nadolink | 250/341.4 |
| 5,892,441 | 4/1999 | Woolley et al. | 340/539 |

*Primary Examiner*—Max Noori
*Attorney, Agent, or Firm*—Alston & Bird LLP

[57] ABSTRACT

The apparatus and associated method of the present invention remotely detects structural defects in a workpiece by monitoring the electrical continuity of thin crack wires deposited on or within the workpiece in response to a communication from a remote interrogation device. As a crack, delamination or other structural defect forms or propagates in a structural member or other workpiece, a crack wire located in the vicinity of the crack breaks. In addition to the crack wires, the defect sensing apparatus includes a transponder and a discontinuity sensor for detecting a discontinuity along the crack wire. In order to inspect the workpiece, a maintenance technician positions a remote interrogation device in proximity with the workpiece under inspection. The interrogation signals provided by the remote interrogation device are received by the transponder and serve to power the defect sensing apparatus. Once sufficiently energized, the discontinuity sensor typically applies a voltage to one end of the crack wire and monitors the voltage level at the other end of the crack wire to determine the crack wire has broken, thereby indicating the presence of a crack, delamination or other defect. The discontinuity sensor reports the crack wire status via the transponder to the remote interrogation device for review by the maintenance technician. The defect sensing apparatus may be integral to a structural member or form one part of a reinforcement patch that is installed during a repair to monitor the structural integrity of a repaired structural member.

12 Claims, 4 Drawing Sheets

REMOTELY INTERROGATABLE APPARATUS AND METHOD FOR DETECTING DEFECTS IN STRUCTURAL MEMBERS

FIELD OF THE INVENTION

The present invention relates to the remote detection of cracks and other defects in structural members.

BACKGROUND OF THE INVENTION

Structural members in aircraft, ships and other equipment may be exposed to considerable stress from a variety of sources, including static and dynamic loading and temperature and pressure variation, and may be subject to further degradation as a result of exposure to corrosive materials and other environmental factors. As a result, the structural members, typically constructed of metal, ceramic or graphite/epoxy laminate materials, may develop structural defects, including the creation or propagation of cracks, delaminations or other defects. These defects may contribute to the catastrophic or other failure of the structural member and hence may pose a threat to human safety or lead to overall equipment failure. As a result, it is important to be able to detect structural defects so as to provide an opportunity to replace or repair structural members before structural failure of the member.

Detection of structural defects in aircraft and other equipment has conventionally been accomplished by periodic visual inspection of structural members exposed to stress. Visual inspection techniques are limited, however, by the need for disassembly to gain access to hidden members, by the difficulty of detecting small defects and by the high labor costs associated with visual inspection.

To overcome the limitations inherent in visual inspection, alternative non-destructive inspection techniques have been developed, including ultrasonic inspection, electrical eddy current inspection, nuclear magnetic resonance (NMR) and radiographic inspection. These alternative techniques, however, typically require sophisticated and costly inspection equipment, highly-skilled technicians, significant disassembly for access, and/or substantial equipment down time.

To avoid the aforementioned limitations, techniques for the detection of cracks and other structural defects have been developed which rely on the deposition of very thin electrically conductive paths or traces ("crack wires") on or within the structural member of interest. See, for example, conventional crack gages such as the Micro-Measurements Crack Detection Gage Model CD-23-50A, Micro-Measurements Crack Propagation Gage Model CPA01 and multiplexable Micro-Measurements Crack Propagation Gage Model CPD01. As defects develop or propagate through the member and across a crack wire, the crack wire is broken. Conventionally, each end of the crack wire extends to the edge or surface of the structural member. In order to detect a structural defect that has broken a crack wire, each end of the crack wire can be physically contacted, such as with a pair of probes, in order to perform a continuity check or resistance measurement.

A number of active monitoring systems have been developed to overcome some of the limitations of inspection-based techniques. For example, an active monitoring system based on mechanically exciting a structure and comparing the measured mechanical response to the excitation to an expected response is disclosed in U.S. Pat. No. 5,195,046. These and other active monitoring systems incorporate complex electromechanical components that require battery power and are typically costly and susceptible to failure.

While crack wires, active monitoring systems and other similar defect detection techniques offer advantages relative to the other aforementioned conventional techniques, significant disassembly may still be required, physical contact with each crack wire must be made, a battery or other source of energy is required, detection hardware is complex and costly and substantial labor costs and equipment down time may still be incurred. Therefore, while a number of defect detection techniques have been developed, it is still desirable to develop improved defect detection techniques which do not suffer from the inherent limitations imposed by prior defect detection techniques, such as disassembly of or other physical contact with the structural member, battery requirements, extensive equipment down time and high labor costs.

SUMMARY OF THE INVENTION

It is thereafter an object of the present invention to provide a remotely interrogatable apparatus for detecting structural defects in a workpiece.

It is a further object of the invention to provide a method for remotely detecting defects within a workpiece.

It is a further object of the invention to provide a patch for repairing a workpiece that incorporates means for thereafter monitoring the repaired workpiece.

These and other objects are provided, according to the present invention, by a remotely interrogatable apparatus and an associated method for detecting cracks, strain, fatigue, excessive temperature, excessive acceleration or other structural defects within a workpiece, such as a structural member or other component of an aircraft. The defect sensing apparatus includes a thin electrically conductive trace ("crack wire") that is deposited on or within a structural member or other workpiece, such as the wing skin of an aircraft. The defect sensing apparatus also includes a communication device having a discontinuity sensor for monitoring the crack wire and a transponder for communicating with both the discontinuity sensor and a remote interrogation sensor, such as a radio frequency (RF) reader. As cracks or other structural defects develop or propagate through the structural member and across a crack wire, the crack wire is broken, thereby creating an electrical discontinuity in the crack wire. Upon interrogation by a remote interrogation device, the discontinuity sensor determines if any of the crack wires have broken and reports the status of the crack wires to the transponder and, in turn, to the remote interrogation device. As such, an inspector can quickly and accurately determine if the respective structural member needs repair or other maintenance.

To minimize maintenance costs and to improve reliability, the remotely interrogatable defect sensing apparatus according to one advantageous embodiment is a passive device that does not include a battery or other energy source, but is, instead, energized by the interrogation signals provided by the remote interrogation device. Once the remotely interrogatable defect sensing apparatus has stored sufficient energy from the interrogation signal, the discontinuity sensor checks for electrical discontinuity along the crack wire and reports to the transponder which, in turn, replies to the remote interrogation device.

According to another advantageous embodiment, the remotely interrogatable defect sensing apparatus is an active apparatus comprising a battery or other energy source. In this energized embodiment, the distance from which the apparatus may interrogated by the remote interrogation device may be increased substantially beyond the distance from which the apparatus of a passive device may be interrogated. In addition, the apparatus of the energized embodiment may include means to actively indicate the existence of a defect. In one instance of such an active indication apparatus, the energized embodiment may include an audible or visible indication of a defect or may communicate the presence of such a defect with a suitable communications receiving device.

According to one advantageous embodiment, the crack wire includes a number of branches extending across different portions of the structural member. According to this embodiment, a crack wire splits from a common first end into a number of branches. The discontinuity sensor preferably detects the electrical continuity of each branch of the crack wire and provides the transponder with a signal indicative of the electrical continuity or discontinuity of each branch for subsequent transmission to the remote interrogation device. Since the branches of the crack wire generally extend across different portions of the structural member, the defect sensing apparatus of this advantageous embodiment not only detects a crack or other defect within the structural member, but also provides information relating to the location of the crack or other defect based upon the specific branch or branches of the crack wire that have been broken by the crack or other defect.

An aircraft or other piece of equipment may include a number of different defect sensing apparatuses mounted upon respective structural members. As such, the transponder of each respective defect sensing apparatus preferably includes a memory device or hardwired or laser-cut register for storing a unique identification number. Upon transmitting information to the remote interrogation device, the transponder preferably also transmits the unique identification number such that the remote interrogation device can identify the defect sensing apparatus that is responding. In addition, the remote interrogation device can be designed to either specifically interrogate individual ones of the defect sensing apparatuses by identifying the defect sensing apparatuses by their respective identification numbers or, alternatively, simultaneously interrogate all of the defect sensing apparatuses within range by transmitting a universal interrogation signal and monitoring the responsive signals for a specific code indicative of the presence of a defect.

According to another embodiment of the present invention, a patch is provided for repairing the workpiece and thereafter monitoring the resulting repaired workpiece. As such, the patch preferably includes the remotely interrogatable defect sensing apparatus including one or more crack wires and a communication device having a transponder and an associated discontinuity sensor. Once the patch has been mounted upon a workpiece to repair and/or reinforce a crack or other defect, the defect sensing apparatus associated with the patch will detect further growth of the crack or other defect which creates an electrical discontinuity by breaking the crack wire. Upon interrogation by remote interrogation device, the defect sensing apparatus associated with the patch will report the electrical discontinuity so that maintenance personnel can make appropriate repairs in a timely fashion without additional growth at the crack or other defect.

Therefore, the remotely interrogatable defect sensing apparatus of the present invention reliably detects cracks, strain, fatigue, over-temperature, over-acceleration, delaminations or other defects within a structural member or other workpiece. Upon interrogation by a remote interrogation device, such as a hand-held RF reader, the defect sensing apparatus will determine if a crack wire has been broken and, if so, will report the electrical discontinuity to the remote interrogation device such that maintenance personnel can make appropriate repairs to the structural member or other workpiece. By permitting remote interrogation, the defect sensing apparatus of the present invention can be quickly interrogated without requiring the inspector to make physical contact with each of the sensors mounted upon the aircraft. In recognition that previously repaired portions of an aircraft or other piece of equipment typically require more frequent monitoring to ensure that the crack or other defect has not continued to grow, the patch of one advantageous embodiment of the present invention includes a remotely interrogatable defect sensing apparatus to permit remote inspection of the repaired portion of a structural member.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Figure 1:
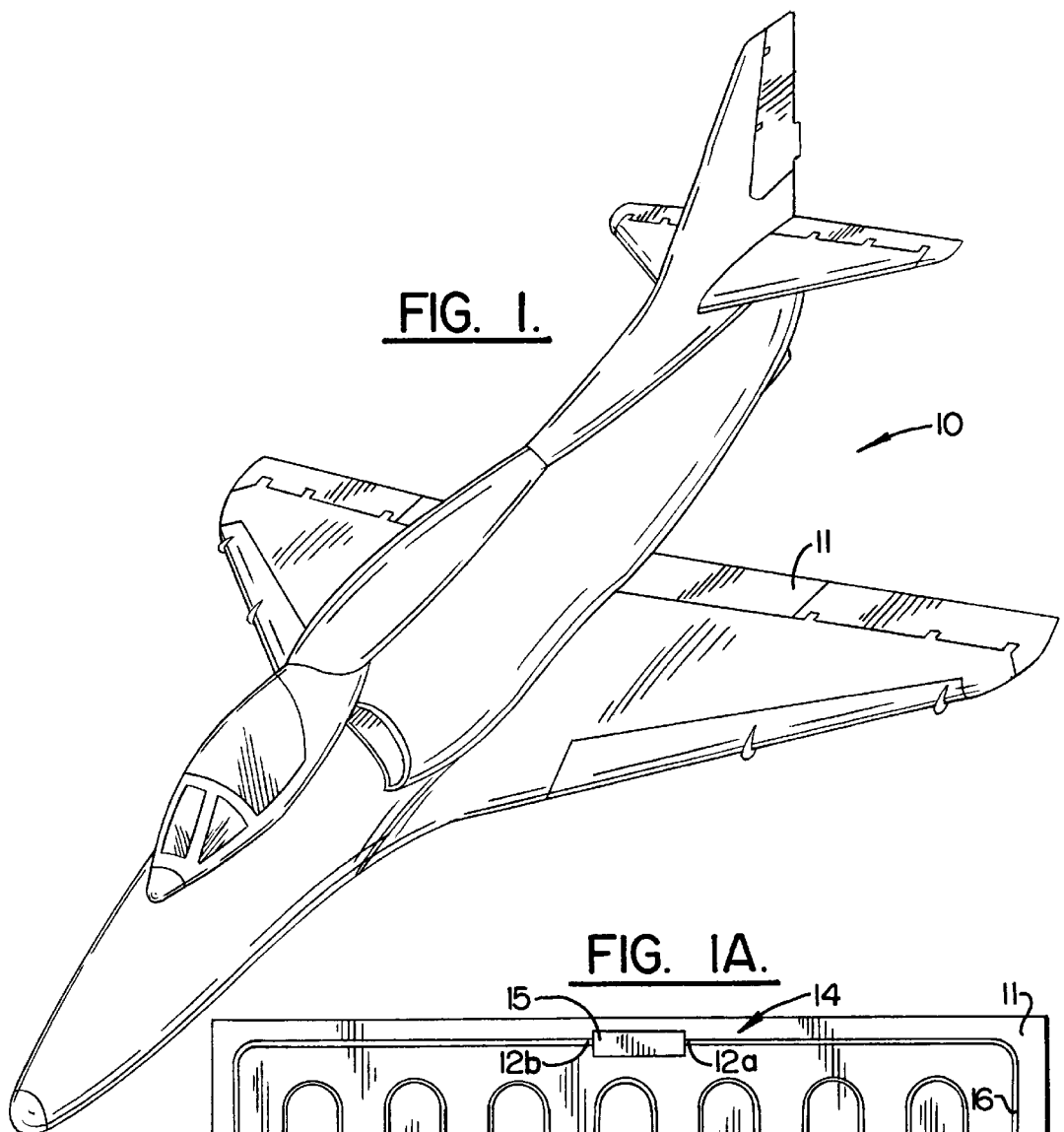
FIG. 1 is a perspective view of an aircraft in which a wing flap that includes the defect sensing apparatus of one embodiment of the present invention is indicated.

Referring now to FIG. 1, an aircraft 10 is shown that includes many different parts or components ("structural members"), such as frame members, wing flaps 11, etc. The structural members of an aircraft can be constructed of a variety of materials, including metal, ceramic or graphite/epoxy laminate materials. Regardless of the materials, structural members are exposed to static and dynamic loading, temperature and pressure variations, corrosive materials and other environmental factors and, as a result, may develop cracks 12, delaminations or other defects that serve to weaken the structure member. As such, the remotely interrogatable defect sensing apparatus 14 of the present invention is designed to detect cracks or other defects in the structural members of an aircraft, ship, helicopter or other pieces of equipment on which the defect sensing apparatus is mounted.

The defect sensing apparatus 14 of the present invention includes one or more thin electrically conductive paths or traces ("crack wires") 16 on or within a respective structural member. The crack wire is preferably deposited, such as via vacuum or gas phase deposition, in a thin layer upon the structural member such that the crack wire will have very low tensile strength. For example, a crack wire typically has a thickness of between about 1000 Angstroms and 50 microns and a width of between a few microns and one-tenth inch. For metallic or other electrically conductive structural members, the crack wire is preferably deposited on the primer layer or on the primer and paint layers so as to be electrically insulated from the conductive structural member. If necessary, an underlying layer of electrically insulating material may be applied. As cracks 12, delaminations or other defects develop or propagate in the structural member in the region underneath or adjacent to a crack wire, the crack wire will break, thereby creating an electrical discontinuity between the first end 12a and the opposed second end 12b of the crack wire. See FIGS. 1A and 1B. As such, the crack wire is preferably deposited to wind back and forth in a sinuous path across the structural member in order to detect defects that occur anywhere in the structural member prior to extensive propagation of the defects. By detecting defects prior to extensive propagation, the defects, such as cracks or delaminations, can be more readily repaired.

Figure 1A:
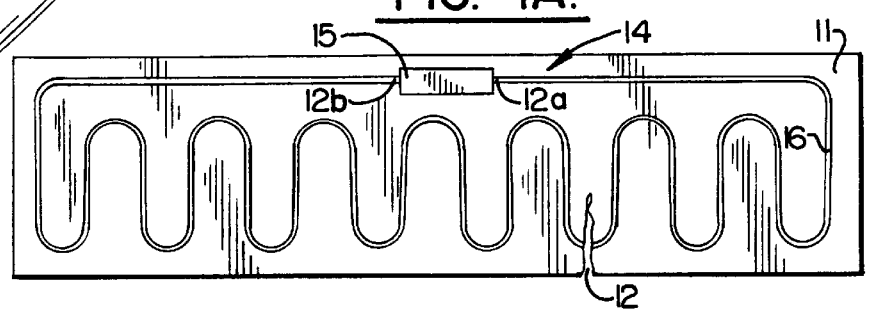
FIG. 1A is a more detailed perspective view of a wing flap of FIG. 1 illustrating one embodiment of the defect sensing apparatus of the present invention that includes a single crack wire that has been broken by a crack in the wing flap.
Figure 1B:
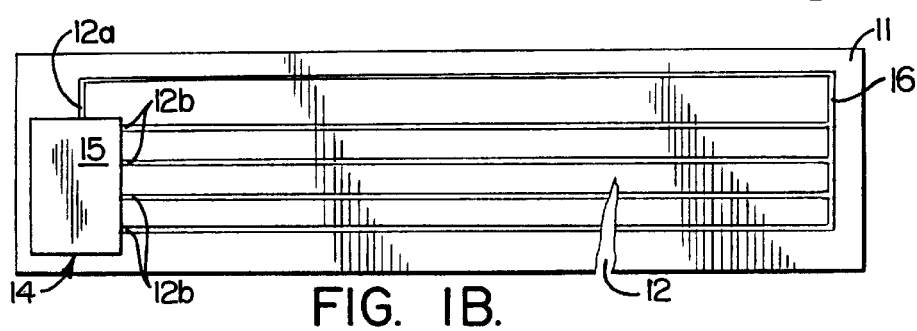
FIG. 1B is a more detailed perspective view of a wing flap of FIG. 1 illustrating another embodiment of the defect sensing apparatus of the present invention that includes a crack wire having a plurality of branches, two of which have been broken by a crack in the wing flap.

Although the crack wire 16 can be a single wire as shown in FIG. 1A, the crack wire can also include multiple wires or a branched structure as shown in FIG. 1B. In the embodiment of FIG. 1B, the crack wire splits into a plurality of branches, each of which extends across a different portion of the structural member. As such, the crack wire of this embodiment has a common first end 12a, but a plurality of second ends 12b. As described below, each branch of the crack wire of this embodiment can be separately analyzed such that the crack wire not only detects defects in the structural member, but also provides information about the relative location of the defect. Alternatively, one or more crack wires may each be a single loop with two ends.

The defect sensing apparatus 14 also includes a communication device 15 including a discontinuity sensor 18 for determining if the crack wire 16 is electrically continuous. For example, the discontinuity sensor typically applies a predetermined electrical voltage at the first end 12a of crack wire and measures the voltage at the second end 12b of crack wire. If the measured voltage at the second end of crack wire is below a threshold level, such as below about 50% of the applied electrical voltage, the discontinuity sensor determines that the crack wire is broken. See FIG. 3.

In the embodiment of FIG. 1B which includes a branched crack wire, the discontinuity sensor 18 preferably applies a predetermined electrical voltage at the common first end 12a and separately measures the voltage at the respective second end 12b of each branch of the crack wire 16. If the measured voltage at the second end of a branch of the crack wire is below a threshold level, the discontinuity sensor detects a break in that branch of the wire. By monitoring a crack wire having a plurality of branches, the defect sensing apparatus 14 can monitor the growth of or change in a crack 12 or other defect. As the crack grows, an increasing number of the branches of the crack wire will break as sensed by the discontinuity sensor and as shown in FIG. 1B.

Although the crack wire 16 could be designed in a variety of manners without departing from the spirit and scope of the present invention, the discontinuity sensor of one embodiment is a discontinuity-based sensor such as one of Micro-Measurements Models CD-23-50A, CPA01 or CPD01.

The communication device 15 of the defect sensing apparatus 14 also includes a transponder 20 for communicating with both the discontinuity sensor 18 and a remote interrogation device 22, such as a hand-held radio frequency (RF) tag reader. For example, the transponder can be a Trovan, TIRIS or Micron MicroStamp tag product that is adapted to transmit the specific RF signals needed to communicate the measurement data. Such data may include header information, sensor information, calibration information and measured data. The data can be as simple as a series of 1s and 0s to represent a closed or open circuit for each individual crack wire path or can be in the form of a varying level to represent a more complex set of data. In addition, the remote interrogation device can be a commercially available or customized reader with the ID and header information replaced by the sensor data stream. This commercial unit can be based on a Trovan Model LID-400, a PEP EasyReader or other similar reader unit.

In operation, an inspector, such as a maintenance technician performing scheduled maintenance on an aircraft 10, can determine the structural integrity of the structural member on which a defect sensing apparatus 14 is mounted by holding the remote interrogation device 22 in the general proximity of the structural member under inspection and initiating a transmission of RF energy from the remote interrogation device to the defect sensing apparatus. Since an aircraft may include several different defect sensing apparatuses mounted on different structural members of the aircraft, such as the various wing flaps, the outer wing frame, the aft box, etc., each transponder 20 preferably includes a memory device 26 for storing a unique identification number. Thus, the remote interrogation device can query a specific defect sensing apparatus by also transmitting the unique identification number of the defect sensing apparatus. Alternatively, the remote interrogation device can simultaneously interrogate all of the defect sensing apparatuses mounted upon the aircraft by transmitting a universal query.

Both the transponder 20 and the discontinuity sensor 18 are preferably passive devices that are energized by the interrogation signal, such as the RF energy, provided by the remote interrogation device 22. By constructing the defect sensing apparatus 14 to be a passive device, the defect sensing apparatus will not require batteries or any other source of energy that would further increase maintenance costs and downtime by having to be periodically inspected and/or replaced.

In one advantageous embodiment, the transponder 20 includes an energy storage capacitor 28 which is charged by the RF energy provided by the interrogation signal. The capacitor thereafter provides energy to operate both the transponder and the discontinuity sensor 18. After the energy stored by the energy storage capacitor reaches a threshold level, the transponder triggers the discontinuity sensor to determine whether the crack wire 16 is electrically discontinuous, such as by applying a predetermined voltage to the common first end 12a of the crack wire and by measuring the voltage at the respective second end 12b of each branch of the crack wire. The discontinuity sensor preferably flags a respective branch of the crack wire as being broken if the voltage measured at the second end of the respective branch of the crack wire is less than a predetermined threshold voltage level, such as 80% of the voltage applied at the first end.

Figure 2:
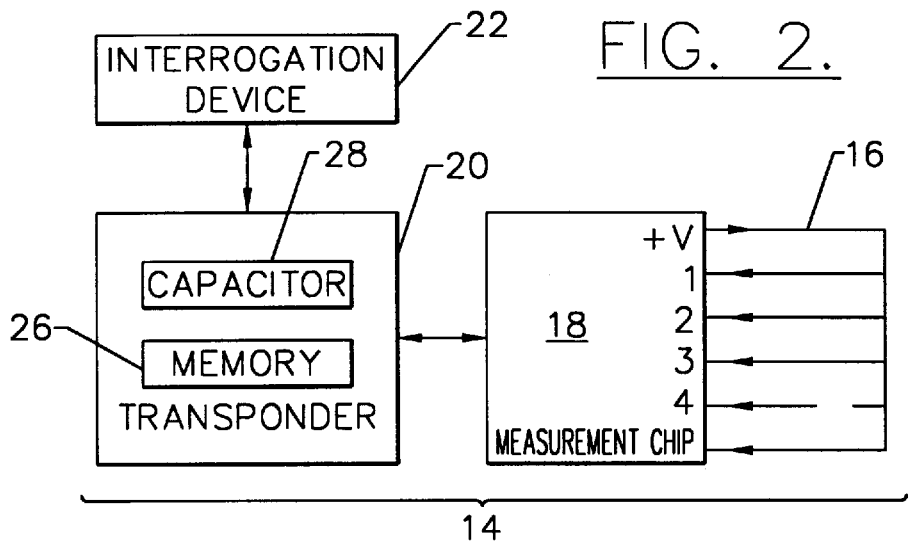
FIG. 2 is a block diagram of one embodiment of the remotely interrogatable defect sensing apparatus depicting a remote interrogation device, a transponder, a discontinuity sensor, and an associated crack wire.
Figure 3:
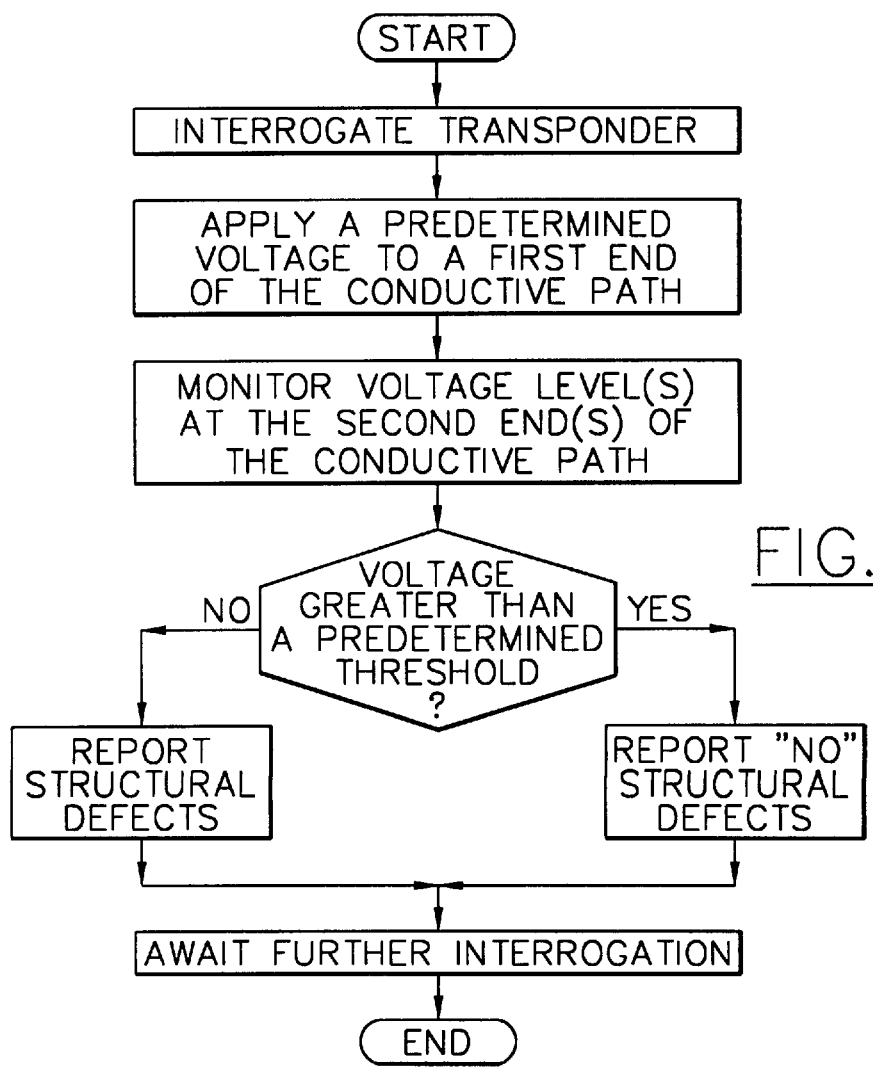
FIG. 3 is a flow diagram illustrating the operations performed to remotely detect defects within a workpiece according to one embodiment of the present invention.

As shown in FIG. 3, the discontinuity sensor 18 then communicates the status of each branch of the crack wire 16 to the transponder 20. The transponder thereafter reports the status of each branch of the crack wire to the remote interrogation device 22 along with the identification number of the defect sensing apparatus 14. Although the status of each branch of the crack wire can be reported in a variety of manners, the discontinuity sensor and the transponder of one advantageous embodiment transmit a digital value with each bit of the digital value associated with a respective branch of the crack wire. Thus, the value of each bit, i.e., 0 or 1, can signify the status of the respective branch of the crack wire, i.e., continuous or discontinuous. By way of example, the digital value 0001 would indicate that the first, second and third branches of the crack wire are continuous and that the fourth branch of the crack wire is broken as shown in FIG. 2.

Figure 2A:
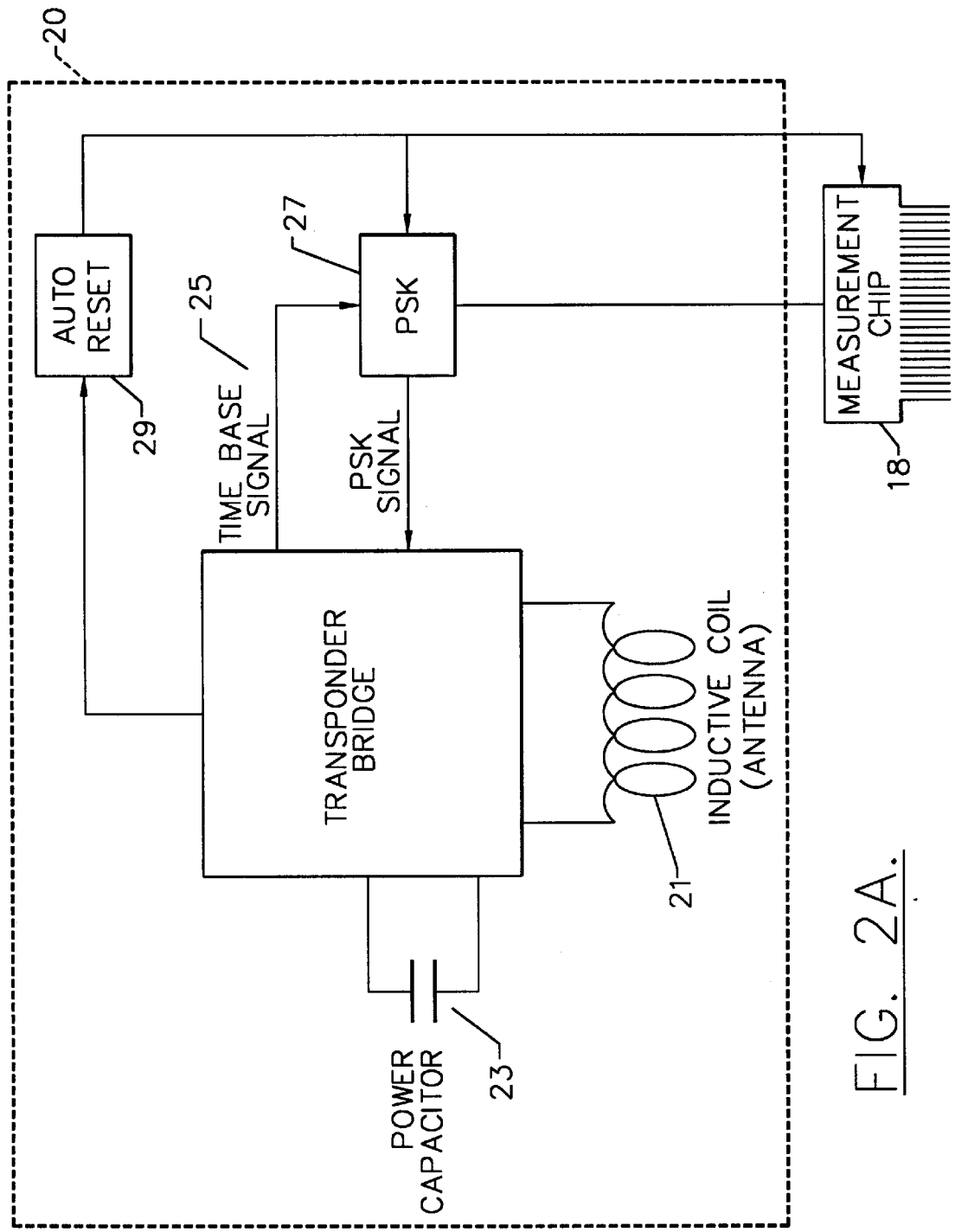
FIG. 2A is a block diagram of one embodiment of the remotely interrogatable defect sensing apparatus detailing a transponder based on phase shift keying (PSK).

In one advantageous embodiment, depicted in FIG. 2A, the transponder 20 is energized by and communicates with remote interrogation device 22 through an inductive coil 21 at an RF frequency such as 125 kHz. Power capacitor 23 is charged by the energy coupled to inductive coil 21 by remote interrogation device 22. The transponder relies on phase shift keying (PSK) to encode defect information on the RF signal providing the report back to remote interrogation device 22. Alternatively, frequency shift keying (FSK) or differential frequency shift keying (DFSK) may be employed instead of PSK.

In the PSK-based system, a time base signal 25 clocks measurement chip 18 to sequentially measure the electrical continuity of each of the crack wires 16. Measurement chip 18 returns the continuity results to PSK circuitry 27 which then sequentially shifts the phase of the RF signal providing the report back to remote interrogation device 22 to indicate crack wire status. Auto reset circuitry 29 is included to initialize transponder 20 and measurement chip 18 upon subsequent interrogations.

The remote interrogation device 22 can store the status report provided by the defect sensing apparatus 14 for subsequent analysis. In addition to storing the status report, the remote interrogation device could also provide an audible tone or a visual indication if a defect was identified such that the inspector could take appropriate remedial action. Alternatively, the remote interrogation device can include a display for providing information to the inspector relating to the presence or absence of a defect such that the inspector could immediately schedule the aircraft 10 for repair.

Figure 4:
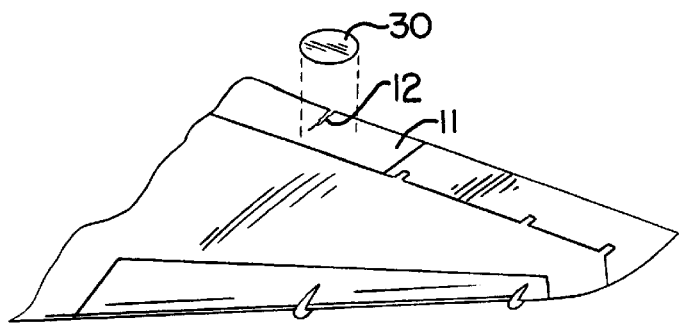
FIG. 4 is a perspective view of an aircraft and a repair patch according to one embodiment of the present invention that will be mounted to a wing flap.
Figure 5:
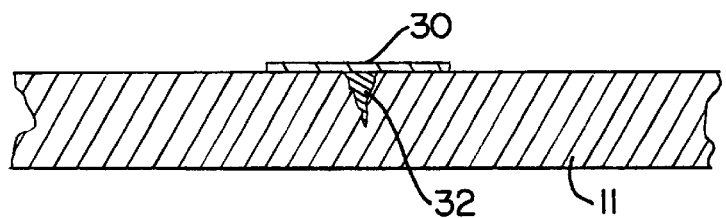
FIG. 5 is an enlarged cross-sectional view of a repair patch affixed over the crack in the wing flap of FIG. 4.

If a crack 12, delamination or other defect is detected, either by use of the defect sensing apparatus 14 of the present invention, by visual inspection, or by any other method, the defect is typically repaired with a patch 30. Patches may be constructed of graphite/epoxy laminate or other suitable materials and are preferably affixed to the structural member with epoxy or other suitable adhesive 32 or by application of energy, such as heat. As shown in FIGS. 4 and 5, patches may be affixed, for example, to a portion of a structural member within which a crack or other defect has developed as a result of exposure to static or dynamic loading or temperature variations.

After a crack 12 or other defect develops in structural member, a patch 30 is affixed with adhesive 32 to the structural member to strengthen structural member and to prevent further propagation of the crack. Since a structural member that has previously developed a defect and has been patched is considered to be more likely to develop further defects, such as the growth of the original crack or the development of new defects, it is quite desirable to monitor the portion of the structural member that has been patched for further defects. As such, a patch can also be used that includes the remotely interrogatable defect sensing apparatus 14 including a transponder 20, a discontinuity sensor 18 and one or more crack wires 16, as described above.

Figure 5A:
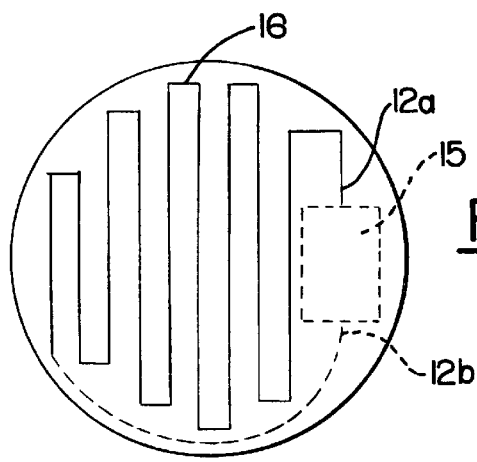
FIG. 5A is a plan view of the underside of the repair patch of FIG. 5 that illustrates the communication device being embedded within the patch and the crack wire being disposed on the lower surface of the patch.

The defect sensing apparatus 14 can be integrally formed on or within the patch 30 either before or after patch is affixed to structural member. Preferably, however, the crack wire 12 is deposited on the lower surface of the patch that is subsequently bonded to the structural member. See FIG. 5A which illustrates the crack wire disposed on the lower surface of the patch. The communication device 15 of the defect sensing apparatus, including the discontinuity sensor 18 and the transponder 20, is preferably disposed within the patch as shown in FIG. 5A, although the discontinuity sensor maintains electrical contact with the crack wire as described above. Once a patch has been affixed to a structural member, further propagation of the crack will break the crack wire, thereby creating an electrical discontinuity. Upon interrogation by a remote interrogation device 22, the defect sensing apparatus of the patch will report the electrical discontinuity such that further repairs can be made to the structural member prior to further disadvantageous growth of the crack or other defect.

Therefore, the remotely interrogatable defect sensing apparatus 14 of the present invention reliably detects cracks 12, delaminations or other defects within a structural member or other workpiece. Upon interrogation by remote interrogation device 22, such as a hand-held RF reader, the defect sensing apparatus will determine if a crack wire 16 has been broken and, if so, will report the electrical discontinuity to the remote interrogation device such that maintenance personnel can make appropriate repairs to the structural member or other workpiece. By permitting remote interrogation, the defect sensing apparatus of the present invention can be quickly interrogated without requiring the inspector to make physical contact with each of the sensors mounted upon the aircraft. In recognition that previously repaired portions of an aircraft 10 or other piece of equipment typically require more frequent monitoring to ensure that the crack or other defect has not continued to grow, the patch 30 of one advantageous embodiment of the present invention includes a remotely interrogatable defect sensing apparatus to permit remote inspection of the repaired portion of a structural member.

It is to be understood that other embodiments of the invention may be easily developed. For example, a temperature tell-tale apparatus may be constructed by replacing the crack wires 16 with wires or solder traces that melt at predetermined temperatures or by controlling thermal mass in the region of the melting wires. Moreover, a strain tell-tale apparatus may be constructed by replacing the crack wires 16 with wires that break at various strain levels and an acceleration tell-tale apparatus may be constructed by replacing the crack wires 16 with wires that are broken by the excursions of a cantilever-supported mass. In addition, a fatigue fuse apparatus may be constructed by replacing crack wires 16 with wires in which have been formed "kinks" or other abrupt changes that break at reduced stress levels.

Many other modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A remotely interrogatable apparatus for detecting structural defects of a workpiece, said apparatus comprising:

a conductive path extending across at least a portion of the workpiece; and a communication device associated with the workpiece, said communication device comprising:

a discontinuity sensor for detecting a discontinuity along said conductive path indicative of a defect within the workpiece; and a transponder, responsive to said discontinuity sensor, for communicating with a remote interrogation device to thereby report structural defects detected within the workpiece.

2. A remotely interrogatable apparatus according to claim 1 wherein said conductive path includes a plurality of branches extending across different portions of the workpiece such that said conductive path extends from a first end common to each of the plurality of branches to a plurality of second ends associated with respective ones of the branches.

3. A remotely interrogatable apparatus according to claim 2 wherein said discontinuity sensor detects a discontinuity along any one of said conductive paths indicative of a defect within the respective portion of the workpiece, and wherein said transponder reports defects detected within any of the different portions of the workpiece.

4. A remotely interrogatable apparatus according to claim 1 wherein said communication device is a passive communication device powered by a remote interrogation signal.

5. A remotely interrogatable apparatus according to claim 1 wherein said communication device further comprises a memory device for storing an identification number assigned to said communication device.

6. A remotely interrogatable apparatus for detecting structural defects of a workpiece, said apparatus comprising:

a conductive path extending across at least a portion of the workpiece, said conductive path including a plurality of branches such that said conductive path extends from a first end common to each of the plurality of branches to a plurality of second ends associated with respective ones of the branches; and a communication device associated with the workpiece and coupled to said conductive path so as to detect a discontinuity along any one of the plurality of branches indicative of a defect within the workpiece, said communication device adapted to communicate with a remote interrogation device to thereby report structural defects detected within the workpiece.

7. A remotely interrogatable apparatus according to claim 6 wherein said communication device comprises:

a discontinuity sensor for detecting the discontinuity along said conductive path; and a transponder, responsive to said discontinuity sensor, for communicating with the remote interrogation device to thereby report structural defects detected within the workpiece.

8. A remotely interrogatable apparatus according to claim 6 wherein said communication device is a passive communication device powered by a remote interrogation signal.

9. A remotely interrogatable apparatus according to claim 6 wherein said communication device comprises a memory device for storing an identification number assigned to said communication device.

10. A method of remotely detecting defects within a workpiece, the method comprising the steps of:

transmitting an interrogation signal from an interrogation device to a remote communication device associated with the workpiece;

detecting a discontinuity along a conductive path in response to the interrogation signal, wherein the conductive path extends across at least a portion of the workpiece and is coupled to the communication device, and wherein the discontinuity is indicative of a structural defect within the workpiece; and reporting a detected structural defect to the remote interrogation device.

11. A method according to claim 10 wherein said detecting step comprises the steps of:

applying a voltage to a first end of the conductive path; and monitoring a voltage level appearing at a second end of the conductive path to determine if the conductive path is continuous.

12. A method according to claim 11 wherein the conductive path includes a plurality of branches such that the conductive path extends from a first end common to each of the plurality of branches to a plurality of second ends associated with respective ones of the branches, and wherein said monitoring step comprises monitoring the voltage levels appearing at each of the second ends of the conductive path to determine if each of the branches is continuous.

* * * * *